United States Patent
Matsushima et al.

(10) Patent No.: US 10,746,726 B2
(45) Date of Patent: Aug. 18, 2020

(54) METHOD FOR ASSESSING THERAPEUTIC EFFECT OF ANTI-CANCER AGENT HAVING ANTI-CD4 ANTIBODY AS ACTIVE INGREDIENT

(71) Applicants: The University of Tokyo, Tokyo (JP); IDAC Theranostics, Inc., Tokyo (JP)

(72) Inventors: Kouji Matsushima, Tokyo (JP); Satoshi Ueha, Tokyo (JP); Satoru Ito, Tokyo (JP); Shoji Yokochi, Tokyo (JP); Yoshiro Ishiwata, Tokyo (JP)

(73) Assignees: THE UNIVERSITY OF TOKYO, Tokyo (JP); IDAC THERANOSTICS, INC., Tokyo (JP)

( * ) Notice: Subject to any disclaimer, the term of this patent is extended or adjusted under 35 U.S.C. 154(b) by 0 days.

(21) Appl. No.: 15/532,465

(22) PCT Filed: Dec. 2, 2015

(86) PCT No.: PCT/JP2015/083855
§ 371 (c)(1),
(2) Date: Jun. 1, 2017

(87) PCT Pub. No.: WO2016/088791
PCT Pub. Date: Jun. 9, 2016

(65) Prior Publication Data
US 2017/0328887 A1   Nov. 16, 2017

(30) Foreign Application Priority Data
Dec. 2, 2014 (JP) ................. 2014-243858

(51) Int. Cl.
| | |
|---|---|
| *A61K 39/00* | (2006.01) |
| *G01N 33/50* | (2006.01) |
| *C12Q 1/68* | (2018.01) |
| *G01N 33/49* | (2006.01) |
| *C12Q 1/04* | (2006.01) |
| *G01N 33/68* | (2006.01) |
| *G01N 33/48* | (2006.01) |

(52) U.S. Cl.
CPC ........ *G01N 33/5011* (2013.01); *C12Q 1/04* (2013.01); *C12Q 1/68* (2013.01); *G01N 33/48* (2013.01); *G01N 33/49* (2013.01); *G01N 33/68* (2013.01); *G01N 2333/525* (2013.01); *G01N 2333/57* (2013.01); *G01N 2333/70503* (2013.01); *G01N 2333/70517* (2013.01); *G01N 2333/70553* (2013.01); *G01N 2333/70578* (2013.01); *G01N 2333/70589* (2013.01); *G01N 2333/70596* (2013.01)

(58) Field of Classification Search
None
See application file for complete search history.

(56) References Cited

PUBLICATIONS

Ueha et al (Cancer Immunol Res 3:631-40, 2015 (Year: 2015).*
Sallusto et al (annu Rev Immunol 22:745-63, 2004 (Year: 2004).*
Nagai et al (J Invest Dermatiol 115:1059-1064, 2000 (Year: 2000).*
Guan et al (J Immunol 183: 172-180, 2009 (Year: 2009).*
Ahmadzadeh et al (Blood 114:1537-1544, 2009 (Year: 2009).*
Schlub et al (J Cell Blol 88:157-164, 2010 (Year: 2010).*
Takata et al (Ji, 177:4330-4340, 2006 (Year: 2006).*
Carney et al., "Circulating HER2 Extracellular Domain: A Specific and Quantitative Biomarker of Prognostic Value in all Breast Cancer Patients?," Biomarkers in Cancer, vol. 5, 2013, pp. 31-39.
Chapman et al., "Improved Survival with Vemurafenib in Melanoma with BRAF V600E Mutation," The New England Journal of Medicine, vol. 364, No. 26, Jun. 30, 2011, pp. 2507-2516.
Choi et al., "Mechanisms Involved in Synergistic Anticancer Immunity of Anti-4-1BB and Anti-CD4 Therapy," Cancer Research, vol. 67, No. 18, Sep. 15, 2007, pp. 8891-8899 (10 pages total).
Finn et al., "Prognostic and Predictive Value of HER2 Extracellular Domain in Metastatic Breast Cancer Treated With Lapatinib and Paclitaxel in a Randomized Phase III Study," Journal of Clinical Oncology, vol. 27, No. 33, Nov. 20, 2009, pp. 5552-5558.
Kwak et al., "Anaplastic Lymphoma Kinase Inhibition in Non-Small-Cell Lung Cancer," The New England Journal of Medicine, vol. 363, No. 18, Oct. 28, 2010, pp. 1693-1703.

(Continued)

*Primary Examiner* — Lei Yao
(74) *Attorney, Agent, or Firm* — Birch, Stewart, Kolasch & Birch, LLP

(57) ABSTRACT

Means that enables monitoring of an anticancer effect of an anti-CD4 antibody or an anticancer drug targeting an immune checkpoint is disclosed. The method for testing a therapeutic effect of a cancer therapy of the present invention is a method for testing a therapeutic effect of an anticancer drug comprising as an effective ingredient an anti-CD4 antibody or an anticancer drug targeting an immune checkpoint, which method comprises investigation of expression of (1) at least one immune checkpoint receptor, (2) CD8, and (3) at least one cell surface molecule selected from the group consisting of CD44 and CD45RO, on T cells using a sample derived from a patient who received the anticancer drug. Induction of a T cell population which is positive for the immune checkpoint molecule (1) and positive for CD8, and which shows high expression of CD44 and/or high expression of CD45RO, indicates that said anticancer drug is producing a therapeutic effect in said patient.

10 Claims, 7 Drawing Sheets

(56) References Cited

PUBLICATIONS

Lennon et al., "Utility of Serum HER2 Extracellular Domain Assessment in Clinical Decision Making: Pooled Analysis of Four Trials of Trastuzumab in Metastatic Breast Cancer," Journal of Clinical Oncology, vol. 27, No. 10, Apr. 1, 2009, pp. 1685-1693.
Liedtke et al., "Breast cancer molecular subtypes—Modern therapeutic concepts for targeted therapy of a heterogeneous entity," Maturitas, vol. 73, 2012, pp. 288-294.
Lièvre et al., "KRAS Mutation Status is Predictive of Response to Cetuximab Therapy in Colorectal Cancer," Cancer Research, vol. 66, No. 8, Apr. 15, 2006, pp. 3992-3995 (5 pages total).
Matsushita et al., "Cancer Exome Analysis Reveals a T Cell Dependent Mechanism of Cancer Immunoediting," Nature, vol. 482, No. 7385, 2012, pp. 1-19.
Shaw et al., "Ceritinib in ALK-Rearranged Non-Small-Cell Lung Cancer," The New England Journal of Medicine, vol. 370, No. 13, Mar. 27, 2014, pp. 1189-1197.
Sias et al., "ELISA for quantitation of the extracellular domain of p185HER2 in biological fluids," Journal of Immunological Methods, vol. 132, 1990, pp. 73-80.
Slamon et al., "Use of Chemotherapy Plus a Monoclonal Antibody Against HER2 for Metastatic Breast Cancer that Overexpresses HER2," The New England Journal of Medicine, vol. 344, No. 11, Mar. 15, 2001, pp. 783-792.
Van Rooij et al., "Tumor Exome Analysis Reveals Neoantigen-Specific T-Cell Reactivity in an Ipilimumab-Responsive Melanoma," Journal of Clinical Oncology, vol. 31, No. 32, Nov. 10, 2013, pp. e439-e442.

\* cited by examiner

METHOD FOR ASSESSING THERAPEUTIC EFFECT OF ANTI-CANCER AGENT HAVING ANTI-CD4 ANTIBODY AS ACTIVE INGREDIENT

TECHNICAL FIELD

The present invention relates to a method for testing a therapeutic effect of an anticancer drug comprising as an effective ingredient an anti-CD4 antibody or an anticancer drug targeting an immune checkpoint.

BACKGROUND ART

Since the advent of molecular-targeted drugs, it is thought that, in order to maximize the effects of the drugs including antibody drugs, utilization of information for selection of the subjects to which the drugs are to be administered or for optimization of their doses, is effective. As a famous example, it is known that expression of the her2/neu molecule may be an aid for selection of breast cancer patients to whom Herceptin (anti-her2/neu antibody drug) is to be administered (Non-patent Document 1), and thus, it is instructed in the FDA's approval that immunohistological testing of the expression level of the her2/neu molecule in pathological diagnosis of a cancer tissue is indispensable for prescription of the drug. A number of similar cases have been reported, and such drugs are increasing year by year. Such indices have come to be called companion diagnosis (biomarkers in a broad sense). Further, it is known that a therapeutic agent for metastatic melanoma (vemurafenib) is highly effective in patients who have a V600E mutation in the BRAF gene (Non-patent Document 2), and thus administration of the agent to patients having this mutation has been recommended in recent years. Furthermore, when an ALK inhibitor (crizotinib, ceritinib) is prescribed to patients with non-small cell lung cancer in whom the kinase is constantly activated as a consequence of fusion between ALK gene and another gene due to translocation of the ALK gene, the presence or absence of the translocation of the ALK gene is determined beforehand (Non-patent Documents 3 and 4). This also corresponds to the companion diagnosis. Unfortunately, it is becoming clear that the ALK fusion gene test has a problem in that, since the position of the cleavage-fusion slightly varies, its detection by RT-PCR with a single primer setting is not always successful.

Approaches supported by the above concept have been taken in prescription of antibody drugs as companion diagnostic drugs, and the authority has approved such approaches. There are the following combinations: Herceptin-her2/neu expression, cetuximab (anti-EGFR)-EGFR expression, and Poteligeo (anti-CCR4)-CCR4 expression. However, in cases of prescription of cetuximab, the expression level of EGFR does not actually reflect the effect, and it has been revealed that a mutation of the K-ras gene present downstream of the EGFR signal actually reflects the effect (Non-patent Document 5). Also in treatment with Herceptin, nearly half of patients who were prescribed the drug showed recurrence/drug resistance (Non-patent Document 6), and therefore improvement is required from the viewpoint of whether or not the expression levels of the target molecules of molecular-targeted drugs can simply be indicators for maximizing the advantages in the patients.

For example, in recent years, antibody drugs that exert their effects especially in the immune system have been shown to be effective in treatment of tumors and cancers in terms of the performance (in particular, the life-prolonging effect) in clinical trials, and the governmental authority gave manufacturing approval to them. Among these drugs, for example, when an anti-CTLA-4 antibody (ipilimumab) was approved by FDA, there was no major discussion on biomarkers. In contrast, for prescription of an anti-PD-1 antibody (nivolumab; Opdivo) approved by the Ministry of Health and Welfare in July 2014, histological staining has been carried out in clinical trials, based on the scenario that testing of the degree of expression of the PD-L1 molecule, which is a ligand of the PD-1 receptor molecule, in cancer patient tissues may be effective. A plurality of companies are working on development of the above-mentioned antibody drugs and companion diagnosis therefor. In this process, problems have become clear. An anti-PD-L1 antibody is used in tissue staining. Studies are carried out using different anti-PD-L1 antibodies, but there is a variation in the thus evaluated effectiveness possibly due to differences in the reactivity among the antibodies. Several problems, such as heterogeneity caused by the fact that the samples are tissues, and possible false-negative results in relation to sampling, have been pointed out. In view of the above, a blood test method with which homogeneity of samples is more likely to be secured is demanded, but there have actually been no biomarkers that were shown to be satisfactory.

Unfortunately, the above-described companion diagnosis (biomarkers) merely provides information on selection of the subjects to be treated, and still cannot be indices for monitoring of whether or not drugs are producing their effects. Moreover, the indices that are most preferred at clinical sites are indices which allow discussion based on blood tests rather than tissue-level indices. A variety of the so-called biomarkers have been reported, but biomarkers primarily demanded at clinical sites still have not been provided so far.

Since Poteligeo (anti-CCR4 antibody) is prescribed for T-cell type blood cancer, the sample to be tested in this case is a blood cell sample, which is relatively homogeneous. However, in solid cancers, the most common method is tissue staining. In recent years, based on the information that the extracellular domain (Extra Cellular Domain; ECD) of the her2/neu molecule is cleaved and released into blood flow, investigation of the level/degree of expression of her2/neu by a blood test targeting ECD has become possible (Non-patent Documents 7 to 10) as an alternative to the test by tissue staining of the molecule immobilized on the cell surface. However, this still remains to be improved.

The past carcinostatic drugs, including not only traditional carcinostatic drugs such as DNA synthesis inhibitors and protein synthesis inhibitors, but also molecular-targeted drugs that have been newly developed recently, directly target molecules such as membrane antigens and enzymes expressed in tumor cells. In contrast, antibody drugs utilized in novel tumor immunotherapies are attracting attention in recent years. Most of the immune checkpoint antibodies such as anti-PD-1 antibodies discussed therefor do not target molecules expressed on tumor cells, but target molecules expressed on immunocompetent cells. Thus, it can be said that the search for biomarkers is now more difficult. The background which makes the situation even more complicated is that, similarly to an anti-PD-1 antibody, an anti-PD-L1 antibody also exhibits a tumor-growth inhibitory effect. That is, it is primarily reasonable to investigate the expression level of the PD-1 molecule in the immunocyte system for prescription of the anti-PD-L1 antibody. When an anti-PD-1 antibody and an anti-PD-L1 antibody become commercially available at the same time, what indices can really be appropriate biomarkers?

There is a group who studied the immune surveillance mechanism against tumors in order to investigate whether the innate immune mechanism in the human body is capable of recognizing and distinguishing tumors, which are cells generated through alteration of autologous cells. The group reported, as a result, that tumors express tumor antigens with which tumor cells can be distinguished from normal cells, and that those antigens are molecules targeted by lymphocytes. For example, it is reported that tumor exome analysis, which is a special technique using next-generation sequencing, was carried out to reveal that the molecule called spectrin-$\beta2$ is targeted by CD8$^+$ T cells (Non-patent Document 11). Such a molecule can also be a biomarker. Similarly, by exome analysis of a tumor tissue from a patient in whom an anti-CTLA-4 antibody was effective, a gene mutation targeted by CD8$^+$ T cells was found (Non-patent Document 12). Thus, such a mutant gene product can also be a biomarker. It may also be possible to infer that, besides biomarkers recognized by CD8$^+$ T cells, which are deduced based on information from the tumor side, molecules responsible for functional regulation of CD8$^+$ T cells can also be biomarkers. That is, functional regulatory molecules such as those expressed in T cells having CTL activity are also likely to be biomarkers. However, the technology gap is still too large to apply such a next-generation sequencing technique to general clinical diagnosis.

It is proposed, as described above, that one possible cause of the immunocompromised state of cancer-bearing patients is the presence of a group of cells expressing immune checkpoint molecules. Recent interest has focused on methods in which functions of such a group of cells are suppressed or eliminated to create conditions where cells and molecules having killer activity against tumors can function, thereby controlling cancers and tumors. It can also be said that the search for biomarkers is even more difficult because of the complicated mechanism. Taking into account the fact that search for biomarkers that reflect therapeutic effects is demanded rather than biomarkers to be used merely as criteria for determining whether drugs are to be prescribed or not, there is an increased difficulty.

PRIOR ART DOCUMENT(S)

Non-Patent Document(s)

Non-patent Document 1: Slamon D J, Leyland-Jones B, Shak S, Fuchs H, Paton V, Bajamonde A, et al. The New England Journal of Medicine. 2001; 344(11): 783-92.
Non-patent Document 2: Chapman P B, Hauschild A, Robert C, Haanen J B, Ascierto P, Larkin J, et al. The New England Journal of Medicine. 2011; 364(26): 2507-16.
Non-patent Document 3: Kwak E L, Bang Y J, Camidge D R, Shaw A T, Solomon B, Maki R G, et al. The New England Journal of Medicine. 2010; 363(18): 1693-703.
Non-patent Document 4: Shaw A T, Kim D W, Mehra R, Tan D S, Felip E, Chow L Q, et al. The New England Journal of Medicine. 2014; 370(13): 1189-97.
Non-patent Document 5: Lievre A, Bachet J B, Le Cone D, Boige V, Landi B, Emile J F, et al. Cancer Research. 2006; 66(8): 3992-5.
Non-patent Document 6: Liedtke C, Kiesel L. Maturitas. 2012; 73(4): 288-94.
Non-patent Document 7: Finn R S, Gagnon R, Di Leo A, Press M F, Arbushites M, Koehler M. Journal of Clinical Oncology: official journal of the American Society of Clinical Oncology. 2009; 27(33): 5552-8.
Non-patent Document 8: Lennon S, Barton C, Banken L, Gianni L, Marty M, Baselga J, et al. Journal of Clinical Oncology: official journal of the American Society of Clinical Oncology. 2009; 27(10): 1685-93.
Non-patent Document 9: Sias P E, Kotts C E, Vetterlein D, Shepard M, Wong W L. Journal of Immunological Methods. 1990; 132(1): 73-80.
Non-patent Document 10: Carney W P, Bernhardt D, Jasani B. Biomarkers in Cancer. 2013; 5: 31-9.
Non-patent Document 11: Matsushita H, Vesely M D, Koboldt D C, Rickert C G, Uppaluri R, Magrini V J, et al. Nature. 2012; 482(7385): 400-4.
Non-patent Document 12: van Rooij N, van Buuren M M, Philips D, Velds A, Toebes M, Heemskerk B, et al. Journal of Clinical Oncology: official journal of the American Society of Clinical Oncology. 2013; 31(32): e439-42.

SUMMARY OF THE INVENTION

Problems to be Solved by the Invention

The present inventors discovered that inhibition of the growth of a solid cancer is possible simply by generally removing CD4-positive cells that are causing an immunodeficiency phenomenon in a cancer-bearing mouse, even without targeting of an immune checkpoint molecule. By using an anti-CD4 antibody having high cytotoxic activity, CD4-positive cells in the body can be removed. It was further revealed that removal of CD4-positive cells promotes infiltration of CD8-positive cells showing killer activity into the tumor, and causes release of those cells into blood. Moreover, combined use of an anti-CD4 antibody and an immune checkpoint antibody produces a more remarkable tumor-growth inhibitory effect as well as an excellent life-prolonging effect.

If a simple index for appropriate evaluation of effectiveness of a drug is available in advance, it becomes possible to consider revision of the dose, combined use of another therapeutic means, switching to another therapeutic means, or the like when no therapeutic effect could be found. For example, such information makes it possible to consider starting of combined use of an immune checkpoint antibody, or, when already used in combination, changing of the type of the immune checkpoint antibody to be used in combination. Also when a therapeutic effect could once been found after starting an anticancer drug treatment but induction of a particular T cell population has become insufficient thereafter, revision of the dose or the like can be similarly considered.

Thus, especially in handling of such a complicated system, an index for evaluation of effectiveness of an anticancer drug that reflects the complex interaction is demanded rather than a biomarker to be used merely for patient selection. An object of the present invention is to provide means that enables monitoring of an anticancer effect of an anti-CD4 antibody or an anticancer drug targeting an immune checkpoint.

Means for Solving the Problems

As a result of intensive study to search for biomarkers for monitoring of an anticancer effect of an anti-CD4 antibody, the present inventors discovered that, in a cancer-bearing living body to which an anti-CD4 antibody was administered, CD8-positive T cells expressing particular surface molecules are grown and killing the tumor cells to suppress the cancer, that is, that the anticancer effect of the anti-CD4 antibody can be monitored by investigating whether or not the CD8-positive T cells expressing the particular surface molecules are induced. The present inventors also discovered that the same method can be used for monitoring of an anticancer effect by use of an immune checkpoint antibody alone as well as an anticancer effect by combined use of an anti-CD4 antibody and an immune checkpoint antibody, thereby completing the present invention.

That is, the present invention provides a method for testing a therapeutic effect of cancer therapy with at least one anticancer drug selected from anticancer drugs comprising as an effective ingredient an anti-CD4 antibody, anticancer drugs comprising as an effective ingredient an antagonist for an inhibitory immune checkpoint molecule, and anticancer drugs comprising as an effective ingredient an agonist for a co-stimulatory immune checkpoint molecule, said method comprising investigating expression of
(1) at least one immune checkpoint receptor;
(2) CD8; and
(3) at least one cell surface molecule selected from the group consisting of CD44 and CD45RO;
on T cells using a sample derived from a patient who received said at least one anticancer drug, wherein induction of a T cell population which is positive for said immune checkpoint molecule mentioned in (1) above and positive for CD8, and which shows high expression of CD44 and/or high expression of CD45RO, indicates that said anticancer drug is producing a therapeutic effect in said patient.

Effect of the Invention

By the present invention, means that enables monitoring of a therapeutic effect of an anticancer drug is provided. According to the method of the present invention, a therapeutic effect of a cancer therapy using an anticancer drug comprising an anti-CD4 antibody as an effective ingredient, an anticancer drug that targets an immune checkpoint molecule (for example, an anticancer drug comprising an immune checkpoint antibody as an effective ingredient), or a combination of these can be evaluated by a test using a blood sample, which shows less variation among samples and which secures higher homogeneity.

BRIEF DESCRIPTION OF THE DRAWINGS

FIG. 6-1 shows the result of flow cytometric investigation of the ratios of PD-1$^+$ cells, CD137$^+$ cells, and CD44$^{hi}$ cells in the CD8$^+$ T cell population in peripheral blood from B16F10 tumor-bearing mice to which either one or both of an anti-CD4 antibody and an immune checkpoint antibody (anti-PD-L1 antibody or anti-PD-1 antibody) was/were administered.

FIGS. 6-2 (B and E) The result of investigation of the ratio of CD44$^{hi}$PD-1$^+$ cells, PD1$^+$ CD137$^+$ cells, or CD44$^{hi}$ CD137$^+$ cells in the CD8$^+$ T cell population in peripheral blood from B16F10 tumor-bearing mice to which either one or both of an anti-CD4 antibody and an immune checkpoint antibody (anti-PD-L1 antibody or anti-PD-1 antibody) was/were administered alone. (C and F) The mean fluorescent intensity (MFI) of PD-1 expression on CD8$^+$ CD44$^{hi}$ PD-1$^+$ cells in peripheral blood. B to D show data obtained when the anti-PD-L1 antibody was administered, and E to G show data obtained when the anti-PD-1 antibody was administered. The data show the mean±standard error for four individuals of mice. A representative result from two independent experiments is shown. *, $P<0.05$; , $P<0.01$; *, $P<0.001$.

MODE FOR CARRYING OUT THE INVENTION

Figure 1:
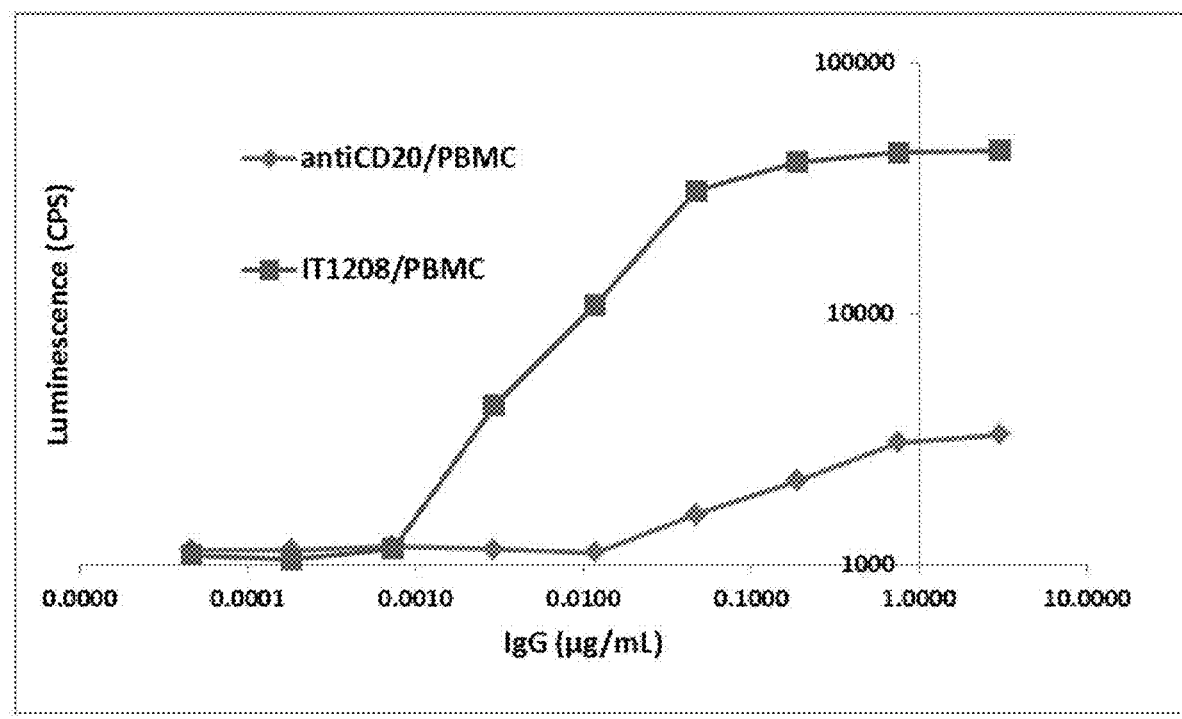
FIG. 1 shows the ADCC activity of an anti-CD4 humanized antibody IT1208 against CD4-positive cells in human peripheral blood mononuclear cells measured by using a commercially-available assay kit.

The patient to be treated by the method of the present invention is a patient receiving cancer therapy by administration of at least one anticancer drug selected from anticancer drugs comprising as an effective ingredient an anti-CD4 antibody, anticancer drugs comprising as an effective ingredient an antagonist for an inhibitory immune checkpoint molecule, and anticancer drugs comprising as an effective ingredient an agonist for a co-stimulatory immune checkpoint molecule. In the present description, an anticancer drug comprising as an effective ingredient an anti-CD4 antibody may be referred to as "anti-CD4 anticancer drug". An anticancer drug comprising as an effective ingredient an antagonist for an inhibitory immune checkpoint molecule, or an anticancer drug comprising as an effective ingredient an agonist for a co-stimulatory immune checkpoint molecule, may be referred to as "immune checkpoint anticancer drug".

In the method of the present invention, expression of the following cell surface molecules (1) to (3) on T cells is investigated using a sample derived from a patient to which the above-described at least one anticancer drug was administered.
(1) At least one immune checkpoint receptor
(2) CD8
(3) At least one cell surface molecule selected from the group consisting of CD44 and CD45RO When induction of a T cell population which is positive for the immune checkpoint receptor (1) and positive for CD8, and which shows high expression of CD44 and/or high expression of CD45RO is detected, the anticancer drug can be judged to be producing a therapeutic effect in the patient. Since all T cells express CD3, the T cell population to be used as an index for the therapeutic effect of the anticancer drug in the method of the present invention is, of course, positive for CD3.

The term "immune checkpoint molecule" includes both receptors and ligands that function as an immune checkpoint. Immune checkpoints are the immune escape mechanism to prevent the immune system from attacking its own body. Immune checkpoint receptors are present on T cells, and interact with immune checkpoint ligands expressed on antigen-presenting cells. T cells recognize an antigen presented on the MHC molecule and are activated to generate an immune reaction, whereas an interaction between immune checkpoint receptor and ligand that occurs in parallel with the above controls the activation of T cells. Immune checkpoint receptors include co-stimulatory receptors and inhibitory receptors, and the T cell activation and the immune reaction are controlled by a balance between both receptors.

In cases where the molecule to be targeted by the immune checkpoint anticancer drug is an immune checkpoint receptor, the immune checkpoint receptor (1) may be the same as or different from the molecule to be targeted by the said anticancer drug.

Specific examples of the immune checkpoint receptor (1) include at least one selected from the group consisting of PD-1, CD137, TIM-3, CTLA-4, BTLA, LAG-3, OX40, and GITR. Preferred specific examples of the immune checkpoint receptor (1) include at least one selected from the group consisting of PD-1, CD137, and TIM-3. Expression of two or more, or three or more of the above-described immune checkpoint receptors may be investigated. Positivity of any kind of immune checkpoint receptor (1) can be judged as indicating the therapeutic effectiveness. CD137 is reported to be expressed in tumor-reactive CD8$^+$ T cells also in human, and TIM-3 is reported to show expression kinetics similar to that of CD137 upon stimulation of T cells. Thus, in the present invention, TIM-3 can be one preferred specific example of the immune checkpoint receptor (1) similarly to CD137. All reports in this field have been analysis of cells infiltrating cancer tissues, and there has been no report showing that a therapeutic effect can be clearly indicated by a blood level.

The CD3$^+$, CD8$^+$, and CD44$^{hi}$ T cell population in mouse is known to be effector or memory cells. It is well known that, in relation to identification of a subpopulation of T cells that will become effector or memory cells in human, mouse CD44 can be regarded as a counterpart molecule in the sense that mouse CD44 is an alternative to human CD45RO. Thus, in cases where a human patient is to be tested, expression of CD45RO alone may be investigated instead of CD44. However, in human, CD44 alone may be investigated, or both CD44 and CD45RO may be investigated.

CD8$^+$ T cells include three subsets, namely, naive cells, effector cells, and memory cells, and memory cells can be divided into two subsets, namely, central memory cells and effector memory cells. Since central memory CD8$^+$ T cells and effector memory CD8$^+$ T cells show antigen-specific activation, they instantly produce cytotoxicity, and the latter shows a stronger activity. Thus, in the present invention, it is especially preferred to investigate whether an effector memory CD8$^+$ T cell population that is positive for the immune checkpoint receptor (1) described above is induced or not.

It is known that effector memory CD8$^+$ cells show decreased expression of adhesion factors such as CCR7 and CD62L, and that effector memory CD8$^+$ T cells are negative for CD45RA (Uchiyama et al., Bulletin of School of Health Sciences, Faculty of Medicine, Niigata University, 10(3), 19-28, 2013-03; Hiroshi Takata and Masafumi Takiguchi, Journal of Immunology, 2006, 177: 4330-4340; and the like). Thus, in the present invention, expression of any one or more of CD45RA, CD62L, and CCR7 on T cells may further be investigated. When induction of a T cell population negative for CD45RA is detected, the anticancer drug can be judged to be therapeutically effective. When induction of a T cell population showing low expression of CD62L is detected, the anticancer drug can be judged to be therapeutically effective. When induction of a T cell population negative for CCR7 is detected, the anticancer drug can be judged to be therapeutically effective. Expression of any two (that is, CD45RA and CD62L; CD45RA and CCR7; or CD62L and CCR7) of the markers may be investigated, or expression of all three markers may be investigated.

As the sample derived from a patient, a blood sample may be preferably used. Blood samples are preferred since they secure higher homogeneity among samples than tissue samples. However, in the method of the present invention, a tumor tissue collected by biopsy or the like may also be used as the sample.

Whether or not a T cell population having a particular pattern of expression of cell surface molecules is grown in the body of the patient can be investigated by, for example, the following methods.

(a) Flow cytometry analysis of a sample derived from the patient.
(b) CD8$^+$ cells in a sample derived from the patient are captured using a support to which an anti-CD8 antibody is immobilized. After washing, the captured cells are reacted at the same time with a plurality of labeled antibodies prepared by binding labeling substances that emit different signals, respectively, to a plurality of antibodies against the cell surface molecules to be measured, and the individual signals are measured/analyzed simultaneously.
(c) A sample derived from the patient is pretreated with an appropriate enzyme such as protease to cleave cell surface molecules at their stem portions, and the released cell surface molecules are measured by multiple ELISA.
(d) mRNAs of cell surface molecules are subjected to multiplex measurement by RT-PCR.

In terms of the flow cytometry analysis mentioned in (a), the analysis method per se is a well-known conventional method, and also concretely described in the following Examples. The antibodies against the cell surface molecules mentioned in (1) to (3) are also known, and commercially available. By using such known antibodies, the flow cytometry analysis can be carried out.

More specifically, for example, from a blood sample collected from the patient, lymphocytes may be collected by a conventional method such as the specific gravity centrifugation method, and then may be reacted with labeled antibodies (usually fluorescently labeled antibodies are used) against the cell surface molecules to be tested, followed by analysis of the reacted lymphocytes using a flow cytometer. As fluorescent dyes for antibodies for flow cytometry, various fluorescent dyes that emit fluorescences having different wavelengths by the same excitation wavelength have been developed and are commercially available. By use of antibodies labeled with such fluorescent dyes, a plurality of cell surface molecules can be simultaneously detected.

The analysis may also be carried out without using separated lymphocytes. That is, a collected blood itself to which an anticoagulant is added may be stained as it is with labeled antibodies, and erythrocytes may then be removed by hemolysis, followed by analysis of lymphocytes using a flow cytometer.

Although expression of cell surface molecules varies among cells, among difference stages of differentiation, and among different stages of activation, immunocompetent cells include a number of relatively homogeneous cell populations (subpopulations) in each of which the intensity of expression of each molecule is fixed within a narrow range. In cases where there is no expression, that is, in cases where the intensity of expression is at the background level, the cell is described as being negative (or −) in terms of the expression. For example, such a cell may be described as CD8$^-$. In cases where a cell shows clearly higher expression than a negative cell, the cell is described as being positive (or +). For example, such a cell may be described as CD8$^+$.

On the other hand, in cases where cells including a plurality of subpopulations are analyzed by flow cytometer, a plurality of intensities of expression may be found even if the same cell surface molecules are expressed. These subpopulations cannot be distinguished from each other/one another in a one-dimensional plot, but they can be distinguished from each other/one another by development into a two-dimensional plot.

In cases where a subpopulation having the highest expression intensity, a negative subpopulation, and a subpopulation having the intermediate expression intensity are plotted, the first subpopulation is described as high (hi, high expression), and the last subpopulation is described as low (lo, low expression). For example, such a subpopulation may be described as CD44$^{hi}$ or CD44$^{lo}$. If there is no difference in the function between a low subpopulation and a negative subpopulation, both of these may also be conventionally comprehensively referred to as Low. For example, a subpopulation negative for expression of CD44 is CD44$^-$. Both CD44$^{hi}$ and CD44$^{lo}$ are CD44$^+$ since these show positive expression.

On the other hand, in cases where there are a number of homogeneous cell populations in each of which the intensity of expression of each molecule is fixed within a narrow range, and where they have one-to-one association with their functions, they are officially recognized as subpopulations. For example, CD44$^{hi}$ CD8$^+$ T cells are CD8$^+$ memory T cells, and CD44$^{lo}$ T cells are naive T cells. Further, when a plurality of cell surface molecules are analyzed in combination by flow cytometry, more complex classification of a large number of subpopulations can be carried out.

In the present invention, the terms "positive", "negative", "high expression", and "low expression" as used in relation to expression of various cell surface molecules have the above-described meanings.

Since various antibodies against the cell surface molecules of (1) to (3) are known as described above, the method (b) can also be carried out using appropriate labeling substances. Examples of the labeling substance include chromophores and fluorescent dyes having different emission wavelengths. Qdot (registered trademark), which is commercially available, and the like may also be preferably used. When dyes having different excitation wavelengths are used, simultaneous measurement can be performed by irradiation with excitation lights having the different wavelengths. The support used for the immobilization of the anti-CD8 antibody may be a support commonly used for immobilization of antibodies or antigens in order to simplify B/F separation in known immunoassay methods. Examples of the support include, but are not limited to, plates and magnetic beads. As the sample derived from a patient, a blood sample may be preferably used.

In the method (c), a sample derived from a patient has to be subjected to a pretreatment to cleave the cell surface molecules to be measured away from the cell surface. Such a pretreatment may be carried out by selecting and using an appropriate enzyme which is capable of cleaving each cell surface molecule away from the cells. For example, CD44 can be cleaved by ADAM17, which is a metalloprotease. The pretreated sample may be subjected to multiple ELISA. As a sample derived from a patient, a blood sample may be preferably used also in this method.

Since the multiplex RT-PCR per se is known, and the mRNA sequences of the cell surface molecules to be measured in the present application are also known, the method (d) may be carried out by using appropriately designed primers. Also in this method, a blood sample may be preferably used as a sample derived from a patient.

Also in the methods (b) to (d), a blood sample may be preferably used as a sample derived from a patient. The expression of each cell surface molecule can be determined as positive, negative, high or low based on a measured value depending on each measurement method. For example, "positive" means that the molecule is expressed, "negative" means that the molecule is not expressed (expressed at a background level or below). Further, according to the measured value, high expression and low expression can be distinguished from each other.

Induction of a T cell population having a particular pattern of expression of cell surface molecules, or an increase in such a T cell population, means that the T cell population detected in a patient after administration of an anticancer drug is larger than that in the patient before the administration of the anticancer drug. Thus, usually, when the present invention is carried out, a sample may also be collected from the patient before the administration of the at least one anticancer drug selected from anti-CD4 anticancer drugs and immune checkpoint anticancer drugs, and the collected sample may be subjected to analysis of the T cell population. After the administration of the anticancer drug has begun, samples may be periodically collected from the patient, and may be subjected to the analysis.

The patient to whom/which the method of the present invention is applied is a mammal which is typically human.

The anticancer drug comprising as an effective ingredient an anti-CD4 antibody is an anticancer drug for solid cancer that was developed as a result of intensive study by the present inventors. This anticancer drug cancels the immunocompromised environment in solid cancer by removal of CD4-positive cells involved in immunosuppression, to promote destruction of cancer cells by CD8-positive CTLs (T cells), thereby producing a therapeutic effect. Furthermore, the anticancer drug can also prevent metastasis and recurrence of solid cancer. In the present invention, the term "anticancer drug" includes suppression of generation (initiation, metastasis, and recurrence) of cancer and suppression of its growth. Accordingly, "anticancer drug" includes therapeutic agents, prophylactic agents, metastasis-suppressing agents, and recurrence-suppressing agents for cancer.

Specifically, the anticancer drug comprising an anti-CD4 antibody as an effective ingredient comprises any of the followings as an effective ingredient. Both of them may be used in combination. In the present description, the effective ingredients (i) and (ii) may be hereinafter collectively referred to as "anti-CD4 component".
(i) An anti-CD4 antibody having a high cytotoxic activity.
(ii) An anti-CD4 antibody or antigen-binding fragment thereof, comprising a cytotoxic component bound thereto.

When a patient to whom/which the test method of the present invention is applied is human, in both cases of (i) and (ii), the anti-CD4 antibody is typically an antibody against human CD4, and is a human-type chimeric antibody, a humanized antibody (prepared by transplanting the CDR region of a non-human-derived antibody to the corresponding region of a human antibody), or a human antibody (the same antibody as an antibody produced in the body of human, which is prepared using a non-human animal or a human cell line).

The cytotoxic activity antibodies have includes the antibody-dependent cell-mediated cytotoxicity activity (ADCC activity) and the complement-dependent cytotoxicity activity (CDC activity). In cases where the anti-CD4 component belongs to (1) above, the anti-CD4 antibody may have any of the ADCC activity and the CDC activity. It is necessary to use an antibody having a high cytotoxic activity that can exert a sufficiently high ability to kill CD4-positive cells.

The term "high cytotoxic activity" in the context of the ADCC activity means that an antibody has a higher ADCC activity than the known anti-CD4 antibody 6G5 or CE9.1 that is known to have an ADCC activity, when the ADCC activity against CD4-expressing cells is measured by a known measurement method. In the context of the CDC activity, the term means that an antibody has a stronger CDC activity than the known anti-CD4 antibody OKT4 that is known to have a CDC activity, when the CDC activity against CD4-expressing cells is measured in an experimental system using the same complements by a known measurement method.

Methods for measurement of the ADCC activity and the CDC activity of antibodies are known and described in e.g. Cancer Immunol. Immunother., 36, 373 (1993), and kits therefor are commercially available. Whether a given antibody has a higher cytotoxic activity than known anti-CD4 antibodies or not may be evaluated using such a commercially available kit. A specific example of measurement of the cytotoxic activity using a commercially available kit is described in the Examples below. The level of the ADCC activity of anti-CD4 antibody can also be evaluated by, as described in the Examples below, mixing human peripheral blood mononuclear cells with the anti-CD4 antibody, allowing the reaction to proceed at 37° C. for several hours, performing flow cytometry analysis to measure the ratio of $CD3^+$ cells to $CD8^+$ cells in the reaction solution, and then comparing the obtained measurement value with a measurement value obtained using an anti-CD4 antibody having no ADCC activity or a known anti-CD4 antibody described above.

Preferably, an anti-CD4 antibody having a high cytotoxic activity has an ADCC activity that is 10 times or more, more preferably 100 times or more higher than the ADCC activity of the known anti-CD4 antibody 6G5 and/or CE9.1, or has a CDC activity that is 10 times or more, more preferably 100 times or more higher than the CDC activity of the known anti-CD4 antibody OKT4. As used herein, the term "10 times or more" means, for example, that the minimum antibody concentration at which a given antibody exhibits a cytotoxic activity against a certain amount of cells is one-tenth or less of that of the above-described known antibody. As for the affinity of the anti-CD4 antibody to CD4, the antibody binding activity $K_D$ may be about $1\times10^{-9}$ M or less.

An anti-CD4 antibody having a high cytotoxic activity can be prepared, for example, from a monoclonal anti-CD4 antibody prepared by a known method or from an already established known anti-CD4 antibody, by increasing the cytotoxicity of the antibody by a method known in the art. In cases where an anti-CD4 antibody that specifically recognizes CD4 expressed on the cell surface and has a strong cytotoxicity is known, such an antibody may be used as an effective ingredient of the agent of the present invention. For example, WO 2010/074266 discloses an anti-CD4 antibody having a higher ADCC activity than conventional anti-CD4 antibodies.

A method per se of producing a monoclonal antibody is a well-known conventional method in the art. For example, when carrying out the well-known hybridoma method, an anti-CD4 monoclonal antibody can be obtained by immunizing an animal (except human) with a CD4 protein or an appropriate fragment thereof (the extracellular region, e.g., a region from the N-terminus to the 394th amino acid of CD4), collecting antibody-producing cells such as spleen cells or lymphocytes from the immunized animal, fusing the antibody-producing cells with myeloma cells to prepare hybridomas, screening a hybridoma which produces an antibody that binds to CD4 protein, growing the hybridoma, and then collecting an anti-CD4 antibody from the culture supernatant. The gene sequence, amino acid sequence, spatial structure, and the like of CD4 have been deposited in public databases under the accession numbers of, for example, M12807 in GenBank of NCBI. The CD4 protein or an appropriate fragment thereof to be used as an immunogen can be easily prepared based on such sequence information according to well-known genetic engineering methods.

Methods for preparing a chimeric antibody, humanized antibody, or human antibody have been also established as well-known methods in the art. For example, an anti-CD4 human antibody can be prepared by using CDR sequence fragments that ensure CD4 recognition prepared by cassette modification method.

Methods for increasing the cytotoxicity of an antibody are also known, and any of these methods may be used. An example of the known methods is described below.

One method for increasing the ADCC activity is the POTELLIGENT (registered trademark) technology, in which fucose (core fucose) contained in sugar chains present in the Fc region of the antibody is removed (Yamane-Ohnuki N, Satoh M, Production of therapeutic antibodies with controlled fucosylation, MAbs2009; 1: 230-236). The enzyme that adds core fucose is encoded by the gene named FucT-8 (Fut-8). Therefore, antibody molecules with enhanced ADCC activity can be obtained by expressing the gene encoding a recombinant antibody in Fut-8 knockout animal cells (Yamane-Ohnuki N, et al., Establishment of FUT8 knockout Chinese hamster ovary cells: an ideal host cell line for producing completely defucosylated antibodies with enhanced antibody-dependent cellular cytotoxicity, Biotechnol Bioeng 2004; 87: 614-622).

Another known example of the method for increasing the ADCC activity is a method in which fucose substrate donation is blocked. However, this method removes all fucose including core fucose, and hence is not specific to core fucose. Thus, the POTELLIGENT (registered trademark) technology described above is more preferred.

Still another example of the method for increasing the ADCC activity is a method in which sugar chains present in the Fc region of the antibody is converted. In this method, addition of core fucose is avoided by introduction of GlcNAc in the antenna-type branched sugar chain region by GnT-III gene manipulation (M. Schuster et al., Improved effector functions of a therapeutic monoclonal Lewis Y-specific antibody by glycoform engineering, Cancer Res 2005; 65: 7934-7941). An anti-CD4 antibody having enhanced ADCC activity prepared by such a method may also be used.

A known example of the method for enhancing the CDC activity is the COMPLEGENT (registered trademark) technology, wherein a part of isotype IgG1 is combined with the sequence of isotype IgG3 to increase the CDC activity (Natsume A, In M, Takamura H, et al. Engineered antibodies of IgG1/IgG3 mixed isotype with enhanced cytotoxic activities, Cancer Res. 2008; 68: 3863-3872).

Another known example is the AccretaMab (registered trademark) technology, wherein the POTELLIGENT (registered trademark) technology and the COMPLEGENT (registered trademark) technology described above are employed in combination to strongly increase the cytotoxic activity of an antibody (Natsume A, et al., Improving effector functions of antibodies for cancer treatment: Enhancing ADCC and CDC, Drug Des Devel Ther. 2009; 3: 7-16). An anti-CD4 antibody wherein both ADCC activity and CDC activity are increased by such a method may also be used.

In cases where an anti-CD4 antibody to which a cytotoxic component is bound is used, the antibody does not need to have a high cytotoxic activity, because CD4-positive cells are injured by the cytotoxic component. An antibody fragment retaining the binding capacity to CD4 (antigen-binding fragment), comprising a cytotoxic component bound thereto, may also be used.

In the present invention, the cytotoxic component means a substance having an activity to destroy living cells, and includes biological toxic substances, chemical substances, and radioactive substances.

The antigen-binding fragment may be any antibody fragment as long as it retains the binding capacity (antigen-antibody reactivity) to the corresponding antigen of its original antibody. Specific examples of the antigen-binding fragment include, but are not limited to, Fab, F(ab')$_2$, and scFv. Fab and F(ab')$_2$ can be obtained, as is well known, by treatment of a monoclonal antibody with a protease such as papain or pepsin. Methods for preparing scFv (single chain fragment of variable region) are also well known. For example, scFv can be obtained by extracting mRNA from a hybridoma prepared as described above, preparing single-stranded cDNA, performing PCR using primers specific to the immunoglobulin H chain and L chain to amplify the immunoglobulin H-chain gene and L-chain gene, linking these using a linker, giving an appropriate restriction enzyme site(s) to the resulting product, introducing the product into a plasmid vector, transforming *E. coli* with the resulting vector to allow expression of scFv, and then recovering the expressed scFv from *E. coli*.

As described above, the test method of the present invention is used for evaluation of a therapeutic effect of a cancer therapy with at least one anticancer drug selected from anti-CD4 anticancer drugs and immune checkpoint anticancer drugs. That is, the test method is used for evaluation of a therapeutic effect of a cancer therapy by administration of an anti-CD4 anticancer drug or an immune checkpoint anticancer drug alone, combined administration of a plurality of immune checkpoint anticancer drugs, or combined administration of an anti-CD4 anticancer drug and one or more immune checkpoint anticancer drugs. However, the patient to whom/which the present invention is applied may also receive combined treatment with another cancer therapy. For example, at least one selected from substances having an action to stimulate cellular immunity or activate NK cells, and immune cell therapy may be further used in combination with the administration.

Cancer cells express a ligand for an inhibitory immune checkpoint receptor, and escape from attack of cytotoxic T cells utilizing the receptor. Therefore, administration of an antagonist against the inhibitory receptor can prevent cancer cells from utilizing the immune checkpoint mechanism, thereby facilitating killing of cancer cells by $CD8^+$ T cells. In addition, administration of an agonist against a co-stimulatory immune checkpoint receptor can enhance the immune reaction, by which killing of cancer cells by $CD8^+$ T cells can also be facilitated. Immune checkpoint anticancer drugs that have received manufacturing approval, such as anti-PD-1 antibody and anti-PD-L1 antibody, are already present and known.

The term "antagonist" includes various substances that interfere with receptor activation induced by binding between receptor and ligand. Examples thereof include substances that interfere with the binding between receptor and ligand by binding to the receptor, and substances that interfere with the binding between receptor and ligand by binding to the ligand.

For example, "an antagonist against an inhibitory immune checkpoint molecule" may be an antagonistic antibody that binds to an inhibitory immune checkpoint molecule (inhibitory receptor or its ligand), a soluble polypeptide that is designed based on an inhibitory immune checkpoint ligand and does not activate the receptor, or a vector capable of expressing such the polypeptide, or the like. Examples of the inhibitory immune checkpoint molecule include receptors such as PD-1, CTLA-4, LAG-3, TIM-3, and BTLA, and ligands such as PD-L1 (ligand for PD-1), PD-L2 (ligand for PD-1), CD80 (ligand for CTLA-4), CD86 (ligand for CTLA-4), GAL9 (ligand for TIM-3), and HVEM (ligand for BTLA). Methods of producing an antibody, and methods of producing a polypeptide by chemical synthesis or genetic engineering procedure are well-known conventional methods in the art, and a skilled person can prepare an antagonist against an inhibitory immune checkpoint molecule as described above by conventional methods.

"An agonist against a co-stimulatory immune checkpoint molecule" may be an agonistic antibody that binds to a co-stimulatory immune checkpoint receptor, a soluble polypeptide that is designed based on a co-stimulatory immune checkpoint ligand and has an effect to activate the receptor, or a vector capable of expressing the polypeptide, or the like. Examples of the co-stimulatory immune checkpoint molecule include receptors such as CD137, OX40, and GITR, and ligands such as CD137L (ligand for CD137), OX40L (ligand for OX40), and TNFSF18 (ligand for GITR).

In cases where the anti-CD4 component is used in combination with an antibody against an immune checkpoint molecule, preferred specific examples of the above-described antagonistic antibody include an anti-PD-1 antibody, anti-CTLA-4 antibody, anti-LAG-3 antibody, anti-TIM-3 antibody, and an anti-BTLA antibody, which antibodies bind to a receptor to inhibit binding of a ligand to the receptor, and preferred specific examples of the above-described agonistic antibody include an anti-CD137 antibody, anti-OX40 antibody, and an anti-GITR antibody, which antibodies bind to a receptor to stimulate a downstream signaling pathway. Preferred specific examples of the antibody also include an anti-PD-L1 antibody, anti-PD-L2 antibody, anti-CD80 antibody, anti-CD86 antibody, anti-GAL9 antibody, and an anti-HVEM antibody, which antibodies bind to a ligand for an inhibitory immune checkpoint receptor to inhibit binding of the ligand to the receptor. The number of the antibody against an immune checkpoint molecule (immune checkpoint antibody) used in combination with the anti-CD4 component is not restricted. One immune checkpoint antibody may be used, or two immune checkpoint antibodies may be used, or three or more immune checkpoint antibodies may be used, in combination with the anti-CD4 component.

Among the above-described antibodies, a preferred antibody that can be preferably used together with the anti-CD4 component may be at least one selected from the group consisting of an antagonistic anti-PD-1 antibody, antagonistic anti-CTLA-4 antibody, antagonistic anti-LAG-3 antibody, antagonistic anti-TIM-3 antibody, antagonistic anti-BTLA antibody, anti-PD-L1 antibody, anti-PD-L2 antibody, agonistic anti-CD137 antibody, agonistic anti-OX40 antibody, and an agonistic anti-GITR antibody; more preferably, at least one selected from the group consisting of an antagonistic anti-PD-1 antibody, antagonistic anti-CTLA-4 antibody, anti-PD-L1 antibody, anti-PD-L2 antibody, agonistic anti-CD137 antibody, and an agonistic anti-OX40 antibody, or at least one selected from the group consisting of an antagonistic anti-LAG-3 antibody, antagonistic anti-TIM-3 antibody, antagonistic anti-BTLA antibody, and an agonistic anti-GITR antibody.

Especially preferred examples include at least one selected from the group consisting of an antagonistic anti-PD-1 antibody, an anti-PD-L1 antibody, and an anti-PD-L2 antibody. A very remarkable anticancer effect can be obtained just by using the anti-CD4 component in combination with at least one selected from an antagonistic anti-PD-1 antibody, an anti-PD-L1 antibody and an anti-PD-L2 antibody, and a still higher therapeutic effect can be obtained by further combining therewith one or more of other immune checkpoint antagonists or agonists or the like (preferred examples include an agonistic anti-CD137 antibody, an agonistic anti-OX40 antibody, an antagonistic anti-CTLA-4 antibody and the like).

Especially preferred examples of the antibody used in combination with the anti-CD4 component also include an antagonistic anti-CTLA-4 antibody. An antagonistic anti-CTLA-4 antibody only may be used in combination with the anti-CD4 component, or one or more of other immune checkpoint antagonists or agonists or the like (preferred examples include an antagonistic anti-PD-1 antibody, an anti-PD-L1 antibody, an anti-PD-L2 antibody, an agonistic anti-CD137 antibody, an agonistic anti-OX40 antibody and the like) may be further combined with the above, by which a still higher therapeutic effect can be obtained.

Especially preferred examples of the antibody used in combination with the anti-CD4 component still further include an antagonistic anti-CD137 antibody. An agonistic anti-CD137 antibody only may be used in combination with the anti-CD4 component, or one or more of other immune checkpoint antagonists or agonists or the like (preferred examples include an antagonistic anti-PD-1 antibody, an anti-PD-L1 antibody, an anti-PD-L2 antibody, an antagonistic anti-CTLA-4 antibody and the like) may be further combined with the above, by which a still higher therapeutic effect can be obtained.

Antibodies against some of immune checkpoint molecules have already been developed, and such known antibodies can be used especially preferably. Specific examples of the preferred combination of antibodies include a combination of three components: the anti-CD4 component, an antagonistic anti-PD-1 antibody and an antagonistic anti-CTLA-4 antibody; and a combination of three components: the anti-CD4 component, an anti-PD-L1 antibody and an antagonistic anti-CTLA-4 antibody, but a combination of antibodies is not limited thereto.

Examples of other substances that can be used in combination with the anti-CD4 component include substances having an action to stimulate cellular immunity or activate NK (natural killer) cells, such as IFN-α/β, IL-12, GM-CSF, and various chemokines (e.g. CCL10, CCL5, RANTES, MIP-1). Combined use of these substances with the anti-CD4 component can further facilitate destruction of cancer cells by the immune system.

Immune cell therapy is a therapeutic method to attack cancer cells using autologous immune cells. Immune cells are taken out of blood or cancer tissue collected or removed from a cancer patient, and cultured in vitro to proliferate and activate them. The immune cells are then recovered and administered to the same patient to attack cancer cells in the patient body. Immune cell therapy that can be used in combination with the anti-CD4 component is not limited, and any of known cell therapies conventionally used to treat cancer may be used. Examples of the immune cell therapy include, but are not limited to, TIL therapy in which lymphocytes present in a tumor tissue (tumor-infiltrating lymphocytes) are isolated, proliferated and then administered; LAK therapy in which lymphocytes mainly containing NK cells are collected from a patient, proliferated and then administered; CTL therapy in which lymphocytes are stimulated using lymphocytes and cancer cells collected from a patient to proliferate CTLs specific to cancer cells of the patient, and then the CTLs are administered; and T cell (chimeric antigen receptor; CAR-T) transfer therapy in which T cells produced by genetic modification are transferred. A still higher therapeutic effect can also be obtained by combined use of the anti-CD4 component and immune cell therapy.

The term "combined use" of certain effective ingredients or drugs, or the term "used in combination" means that a plurality of effective ingredients are administered concurrently, sequentially, or separately, to a patient. A plurality of effective ingredients to be used in combination may be provided as separate formulations. In cases where they are administered concurrently, a plurality of effective ingredients may be contained in a single formulation.

The administration route of the anti-CD4 component may be oral or parenteral, and parenteral administration such as intramuscular administration, subcutaneous administration, intravenous administration, or intraarterial administration is preferred. The anti-CD4 component may be administered locally to the vicinity of solid cancer tissue, or may be administered to a regional lymph node in the vicinity of solid cancer, and systemic administration is preferred. The above-described administration routes are also applied to other substances used in combination with the anti-CD4 component.

The anti-CD4 component may be administered at any dose as long as it is effective for therapy of solid cancer to be treated. The effective dose is appropriately selected depending on tumor size, symptoms, age and body weight of the patient, and the like. The dose of the anti-CD4 component may be, but not limited to, about 0.001 mg/kg to 1000 mg/kg, e.g., about 0.01 mg/kg to 100 mg/kg, in terms of the weight of the effective ingredient per day per 1 kg body weight of the patient. The above-described dose may be given to a patient once or dividedly in a few or several times in a day. During the treatment period, the anti-CD4 component may be administered once, or daily for a few or several days, or may be administered multiple times every few or several days, every few or several weeks, or every few or several months.

The dose of the antagonist against the immune checkpoint molecule is also appropriately selected depending on tumor size, symptoms and the like. Usually, a desirable effect is obtained by increasing the total dose and the frequency of administration of the antagonist more than those of the anti-CD4 component. In cases where an antibody against the immune checkpoint molecule is used as an antagonist, the antibody may be given to a patient at a dose of ⅕ to 5 times the dose of anti-CD4 component per single administration, and at a frequency of 3 to 10 times or more the frequency of administration of anti-CD4 component. Administration of the antagonist may be continued long-term. In cases where single administration of anti-CD4 component and a few or several administrations of antagonist are used in combination, the administration of antagonist can be started before, at the same time as, or after the administration of anti-CD4 component. When an agonist against the immune checkpoint molecule is used in combination with anti-CD4 component, the dose etc. of the agonist may be the same as those of the antagonist.

Other substances and therapies that may be used in combination with anti-CD4 component may be used in the same manner as when they are used alone in cancer therapy.

It is also possible to reduce the dose, the frequency of administration, the dosing period, etc. of drugs, since an increased effect is obtained thanks to combined use with anti-CD4 component.

The anti-CD4 component and other substances that may be used in combination therewith can be formulated by appropriately mixing with additives such as pharmaceutically acceptable carriers, diluents, and/or excipients that are suitable for the administration route employed. Examples of the formulation include oral preparations such as tablets, capsules, granules, powders and syrups; and parenteral preparations such as inhalants, injection solutions, suppositories and solutions. Formulation methods and additives which can be used are well known in the field of formulation of pharmaceuticals, and any of the methods and additives may be used.

When achievement of a therapeutic effect could be confirmed by the method of the present invention, effective treatment, prevention of metastasis, and/or prevention of recurrence of cancer is/are possible by continuing the anticancer drug administration that has been carried out for the patient. The term "therapeutic effect" includes a metastasis-preventing effect and a recurrence-preventing effect. For example, if a patient is being treated by combined administration of an anti-CD4 anticancer drug and an immune checkpoint anticancer drug, a desired therapeutic effect can be obtained by continuing the combined administration.

When no therapeutic effect could be found, revision of the dose of the anticancer drug, combined use of another therapeutic means, switching to another therapeutic means, or the like can be considered. For example, it is possible to consider starting of combined use of an immune checkpoint anticancer drug(s) if the patient has been receiving administration of an anti-CD4 anticancer drug alone, or to consider changing of the type or dose of the immune checkpoint anticancer drug if the patient has already been receiving the combined administration. Also when a therapeutic effect could once been found after starting an anticancer drug treatment but induction of a particular T cell population has become insufficient thereafter, revision of the dose or the like can be similarly considered.

EXAMPLES

The present invention is described below by way of Examples more concretely. However, the present invention is not limited to the Examples described below.

1. Preparation of Anti-CD4 Humanized Antibody Having High ADCC Activity

According to the method described in WO 2010/074266, an anti-human CD4 humanized antibody IT1208 having enhanced ADCC activity (wherein HV2 and LV0 described in WO 2010/074266 are contained as the variable region; subtype, IgG1) was prepared. The antibody binding activity as measured using Biacore T100 was $K_D$ (nM)<0.009, which indicates high binding activity.

Measurement of the ADCC activity of IT1208 was carried out under the following conditions, according to the protocol for an ADCC activity assay kit sold by Promega. After gently mixing 12,500 PBMCs derived from a healthy individual, anti-CD4mAb (IT1208), and 75,000 ADCC Bioassay Effector cells contained in the Promega kit, the cells were cultured in a $CO_2$ incubator at 37° C. for 6 hours. The luminescent reagent Bio-Glo reagent was added to the culture, and culturing was then continued at room temperature for 20 minutes, followed by measuring chemiluminescence using a luminescence plate reader.

The results are shown in FIG. 1. IT1208 showed ADCC activity at 1 nM or more, and the activity then increased concentration-dependently to reach the maximum value at 50 nM. In the cases of Rituximab (antiCD20), which was used as a control antibody, the concentration at which the ADCC activity began to be found was 10 nM or more, and the concentration at which the maximum value was achieved was 1 µM or more.

2. Action Mechanism of Antitumor Effect by Use of Anti-CD4 Antibody Alone, Use of Immune Checkpoint Antibody Alone, or Combined Use of Anti-CD4 Antibody+Immune Checkpoint Antibody The mouse melanoma cell line B16F10 ($5 \times 10^5$ cells/mouse) was subcutaneously transplanted into the right abdomen of C57BL/6 mice (female, 7 weeks old), and antibody administration was carried out as described below (Day 0=day of cancer cell transplantation).

TABLE 1

| | |
|---|---|
| Negative control group | No antibody is administered. |
| Anti-CD4 alone group | An anti-CD4 antibody (0.2 mg; GK1.5) is intraperitoneally administered twice on Day 5 and Day 9. |
| Anti-PD-L1, anti-PD-L2, anti-OX40, or anti-CTLA-4 alone group | An anti-PD-L1 antibody (10F.9G2, manufactured by BioXcell), anti-PD-L2 antibody (TY25, manufactured by BioXcell), anti-OX40 antibody (OX-86, agonist antibody; manufactured by BioXcell), or anti-CTLA-4 antibody (9D9, antagonist antibody; manufactured by BioXcell) is intraperitoneally administered at a dose of 0.2 mg on Day 4, Day 8, Day 14, and Day 18, four times in total. |
| Anti-CD4 + anti-PD-L1, anti-PD-L2, anti-OX40, or anti-CTLA-4 combination group | An anti-CD4 antibody (0.2 mg) is intraperitoneally administered twice on Day 5 and Day 9, and an anti-PD-L1, anti-PD-L2, anti-OX40, or anti-CTLA-4 antibody is administered at a dose of 0.2 mg on Day 4, Day 8, Day 14, and Day 18, four times in total. |
| Anti-CD8 alone group | An anti-CD8 antibody (0.2 mg; YTS169.4) is intraperitoneally administered twice on Day 5 and Day 9. |
| Anti-CD4 + anti-CD8 combination group | An anti-CD4 antibody (0.2 mg; GK1.5) is intraperitoneally administered twice on Day 5 and Day 9, and an anti-CD8 antibody (0.2 mg; YTS169.4) is intraperitoneally administered twice on Day 5 and Day 9. |

Figure 2:
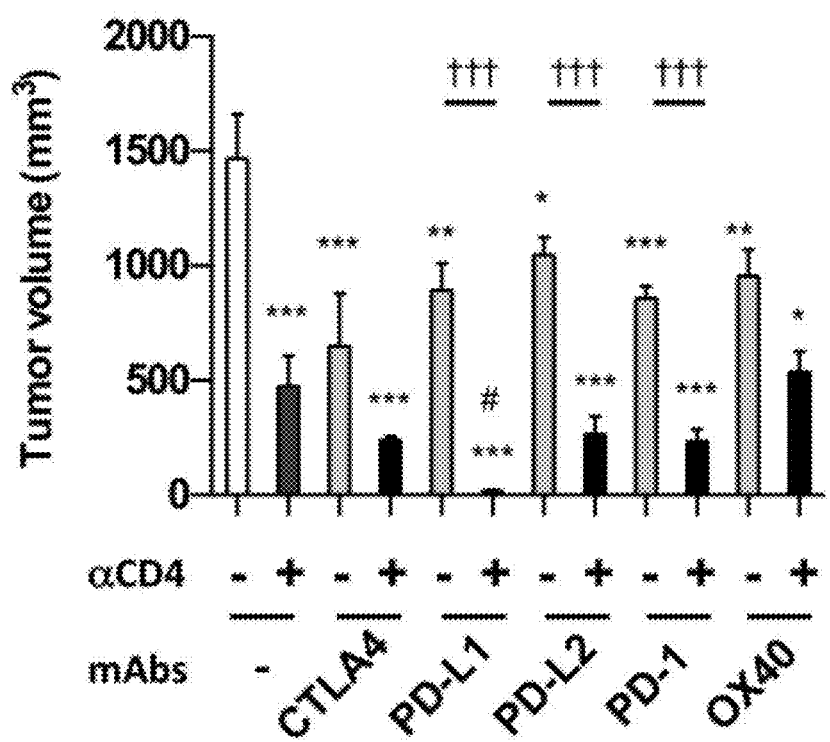
FIG. 2 shows the tumor volume in each group of C57BL/6 mice transplanted with the B16F10 cell line. The tumor volume was calculated (short diameter×short diameter×long diameter×π/6) from the solid tumor diameter measured on Day 16. Significant difference from the tumor control group (without antibody administration: αCD4−, mAbs−): *, $p<0.05$; , $p<0.01$; *, $p<0.001$. Significant difference from the group in which an anti-CD4 antibody (clone GK1.5) was administered alone (αCD4+, mAbs−): #, $p<0.05$. Significant difference between each group in which an immune checkpoint antibody was administered alone (αCD4−, mAbs+) and a group in which an anti-CD4 antibody was used in combination (αCD4+, mAbs+): ††, $p<0.001$.

FIG. 2 shows the tumor volume in each group of C57BL/6 mice (anti-CD4 alone group, immune checkpoint antibody alone group, and combination group of these antibodies) transplanted with the B16F10 cell line. The tumor volume was calculated (short diameter×short diameter×long diameter×π/6) from the solid tumor diameter measured on Day 16.

The anti-CD4 antibody significantly inhibited the growth of the solid tumor of B16 melanoma to about ⅓ relative to that in the control group (Dunnett; significance level, $p<0.01$). Here, based on observation of the tumor-growth inhibitory effect by the use of each agent alone, it is clearly shown that the anti-CD4 antibody has a better inhibitory effect than the other immune checkpoint antibodies when used alone.

When the anti-PD-L1 antibody, anti-PD-L2 antibody, anti-OX40 antibody, and anti-CTLA-4 antibody were individually administered, significantly stronger inhibition of the growth could be observed relative to the growth in the control group (Dunnett; significance level, $p<0.01$), although the inhibition was weaker than that by the anti-CD4 antibody. When the anti-CD4 antibody was used in combination with the anti-PD-L1 antibody, anti-PD-L2 antibody, anti-OX40 antibody, or anti-CTLA-4 antibody, the growth of the B16 melanoma solid tumor was more strongly inhibited than in the groups in which the antibodies were individually administered without administration of the anti-CD4 antibody. The averages in the immune checkpoint antibody alone groups were significantly different from the averages in the anti-CD4 combination groups (Dunnett; significance level, $p<0.05$ or $p<0.01$). Thus, synergistic effects by the combinations became apparent. In particular, the average tumor volume in the anti-CD4+anti-PD-L1 combination group was significantly different from that in the anti-CD4 alone group (significance level, 5%; Dunnett). Thus, a remarkable synergistic effect by the combined use of the anti-CD4 antibody and the anti-PD-L1 antibody was shown.

Figure 3:
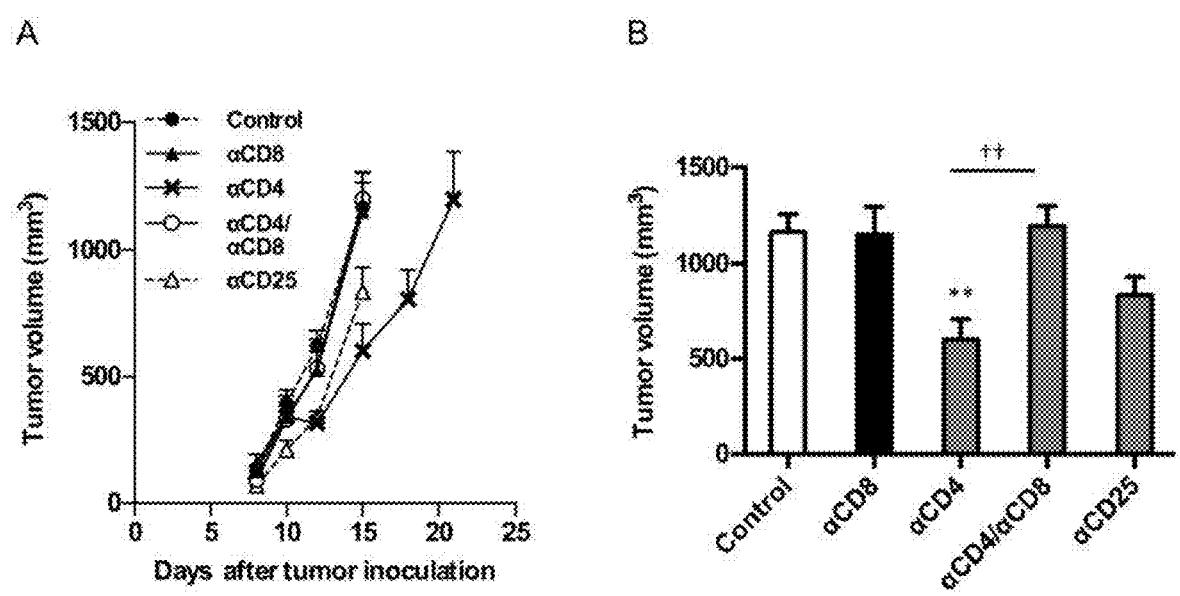
FIG. 3 shows the result of investigation of the tumor volume in B16F10 tumor-bearing mice to which an anti-CD4 antibody or an anti-CD8 antibody was administered alone, or these antibodies were administered in combination. Significant difference from the tumor control group (without antibody administration: αCD4−, mAbs−): **, $p<0.01$. Significant difference between each group in which an immune checkpoint antibody was administered alone (αCD4−, mAbs+) and a group in which an anti-CD4 antibody was used in combination (αCD4+, mAbs+): ††, $p<0.01$.

FIG. 3 shows the result of study on combined use of an anti-CD4 antibody and an anti-CD8 antibody. The tumor volume was calculated in the same manner as described above. FIG. 3B shows the result of comparison of the tumor volume on Day 15.

As shown in FIG. 3, administration of the anti-CD8 antibody together with the anti-CD4 antibody caused complete disappearance of the antitumor action of the anti-CD4 antibody. It became clear that CD8-positive T cells, that is, cytotoxic T cells (CTLs), largely contribute to the action mechanism of the anti-CD4 antibody.

C57BL/6 mice in each group transplanted with the B16F10 cell line were sacrificed on Day 14, and the tumor was removed. From part of the tumor tissue, intratumor lymphocytes were separated, and the separated lymphocytes were analyzed using a flow cytometer. Part of the remaining tumor tissue was used for preparation of tissue sections. The procedure was as follows.

An anti-CD45.2 antibody was intravenously injected into each mouse, and the tumor tissue was separated 3 minutes later. The tumor tissue was minced with scissors, and then treated with collagenase, followed by obtaining intratumor lymphocytes by the specific gravity centrifugation method.

The intratumor lymphocytes were stained with an anti-CD45 antibody, anti-CD11b antibody, anti-CD19 antibody, anti-NK1.1 antibody, and anti-CD8 antibody, and the $CD8^+$ T cell population in the tumor parenchymal tissue which is $CD11b^- CD19^- NK1.1^- CD8^+$ (hereinafter this population is referred to as $CD8^+$ T cells) contained in lymphocytes in the tumor parenchymal tissue ($CD45^+$ IVS $CD45.2^-$) was analyzed by flow cytometry. Further, staining with an anti-CD45 antibody, anti-CD11b antibody, anti-CD19 antibody, anti-NK1.1 antibody, anti-CD8 antibody, anti-PD-1 antibody, and anti-CD137 antibody was carried out to analyze $PD-1^+ CD137^+ CD8^+$ T cells.

Further, CD8 T cells were subjected to stimulation culture with PMA and ionomycin, and stained with an anti-IFNγ antibody and an anti-TNFα antibody, to analyze $IFNγ^+ TNFα^+ CD8^+$ T cells.

Before the staining with the antibodies described above, Fc receptors were blocked with an anti-mouse CD16/CD32 antibody (clone 2.4G2, BioXcell). The measurement was carried out with Gallios (Beckman Coulter), followed by analysis using FlowJo software (version 9.7.5; FlowJo, LLC). Dead cells were removed by staining with propidium iodide (PI).

The tumor tissue was embedded in Tissue-Tek OCT compound (Sakura Finetek), and frozen in liquid nitrogen. Tissue sections with a thickness of 6 µm were prepared, and then subjected to blocking of nonspecific reaction using Blocking One (Nacalai Tesque, Inc.), followed by staining with an anti-CD8 antibody, anti-ΔhLNGFR (truncated form of human low-affinity nerve growth factor receptor) antibody, and propidium iodide.

Thereafter, the tissue sections were embedded using the Prolong Gold reagent (Life Technologies), and immunostaining images were observed using an SP5 confocal microscope (Leica Microsystems).

Figure 4:
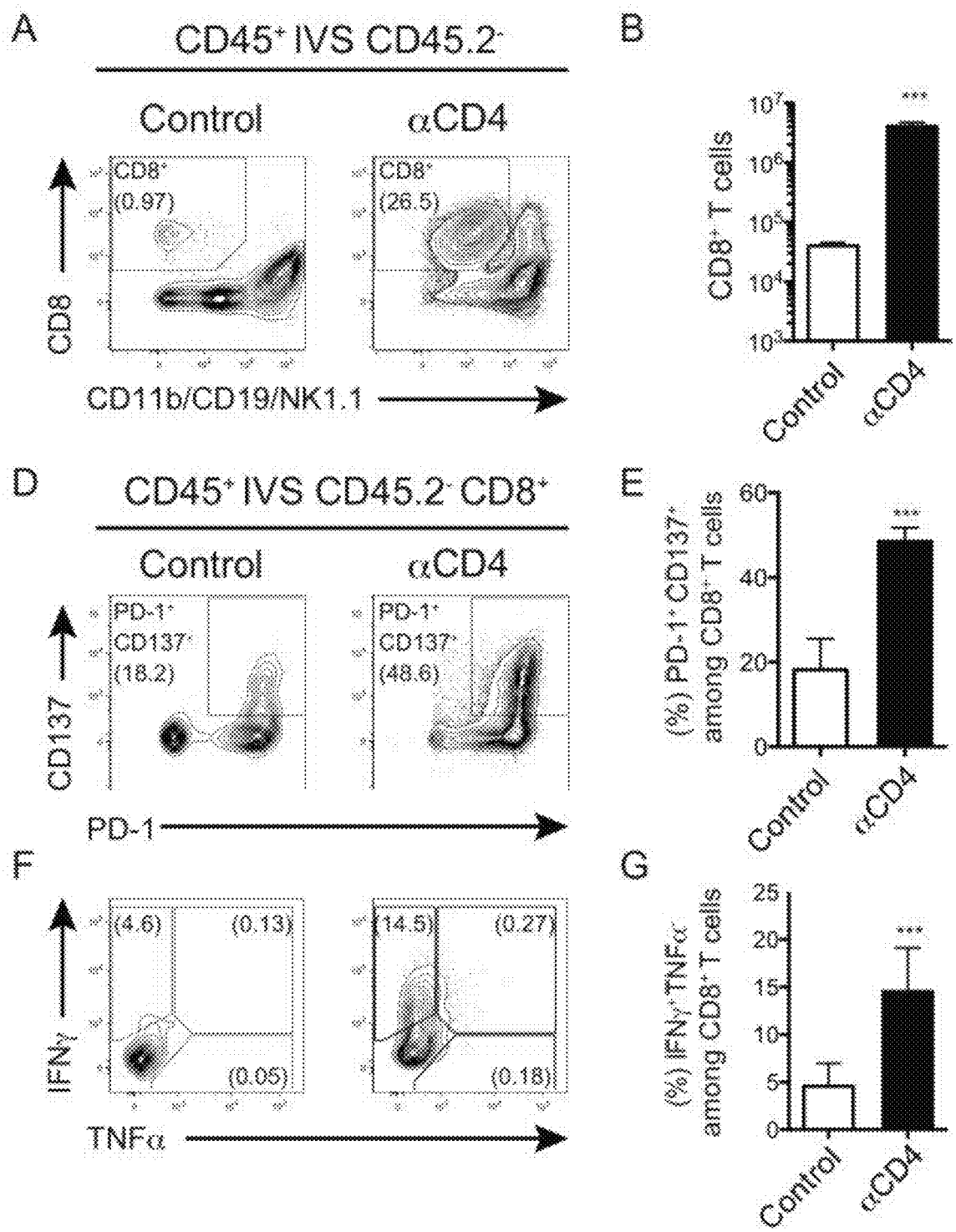
FIG. 4 A fluorescent dye-labeled anti-CD45.2 antibody (clone 104) was intravenously administered to each mouse transplanted with a B16F10 tumor to stain CD45-positive cells circulating in peripheral blood in advance (intravascular staining (IVS) method). Three minutes thereafter, the tumor was collected, and the tumor tissue was loosened, followed by separating a lymphocyte-rich cell population. First, the cells were stained with an anti-CD45 antibody (clone 30-F11) that was different from the anti-CD45.2 antibody, as well as with an anti-CD11b antibody (clone M1/70), anti-CD19 antibody (clone 1D3), anti-NK1.1 antibody (clone PK136), and anti-CD8 antibody (clone 53-6.7), for identification of lymphocytes that were positive for CD45 (lymphocytes) and negative for anti-CD45.2 in the (non-intravascular) tumor parenchymal tissue (CD45$^+$ IVS CD45.2$^-$). Among these, a CD8$^+$ T cell population in the tumor parenchymal tissue which was CD11b$^-$ CD19$^-$ NK1.1$^-$ CD8$^+$ was analyzed by flow cytometry (A, B). Further, for the CD8$^+$ T cell population, expression analysis of PD-1 and CD137 (D, E) was carried out by staining with an anti-PD-1 antibody (clone RMP1-30) and an anti-CD137 antibody (clone 17B5) immediately after the separation, or expression analysis of IFNγ and TNFα (F, G) was carried out by staining with an anti-IFNγ antibody (clone XMG1.2) and an antibody TNFα antibody (clone MP6-XT22) after stimulation culture with PMA and ionomycin. The values shown in the flow cytometry plots (A, D, F) indicate the mean frequencies in the parent population. B, E, and G show bar graphs showing the frequencies of CD8$^+$ T cells, and PD-1$^+$ CD137$^+$ cells or IFNγ$^+$ TNFα$^+$ cells among the CD8$^+$ T cells. The data show the mean±standard error for four individuals of mice. A representative result from at least four independent experiments is shown. ***, significant difference at $p<0.01$.

As shown in FIG. 4B, the anti-CD4 antibody significantly potentiated intratumor CD8-positive cells 27-fold relative to those in the control group (Dunnett; significance level, p<0.01). Further, PD-1$^+$ CD137$^+$ CD8$^+$ T cells and IFNγ$^+$ TNFα$^+$ CD8$^+$ T cells also increased 2.7-fold and 3.2-fold, respectively (FIG. 4E, G). That is, an increase in especially CD8$^+$ CD44$^{hi}$ CD62L$^{lo}$ PD-1$^+$ CD137$^+$ cells occurred in response to depletion of CD4-positive cells by the anti-CD4 antibody in the mice.

Figure 5:
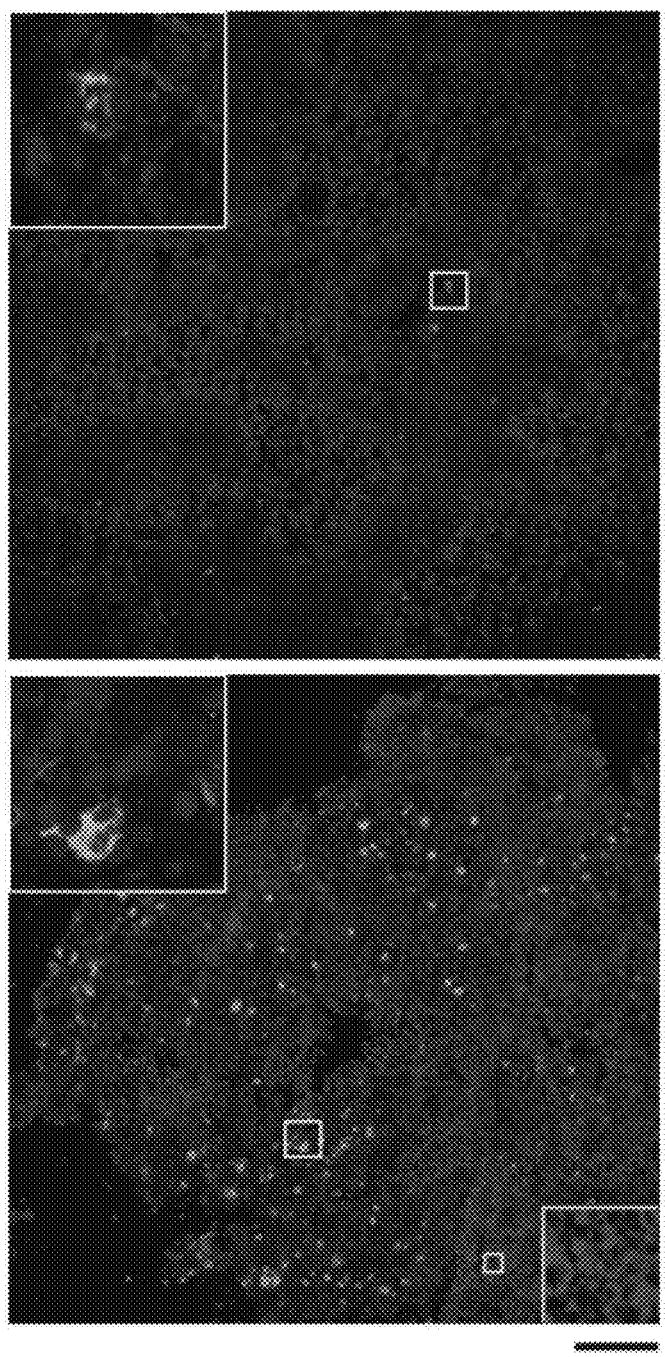
FIG. 5 shows the result of immunostaining of a tumor tissue in a B16F10 tumor-bearing mouse to which an anti-CD4 antibody was administered, which immunostaining was carried out using a fluorescently labeled anti-CD8 antibody and anti-LNGFR antibody.

On the other hand, analysis of the tumor tissue sections by the immunohistological method revealed an evident increase in intratumor CD8-positive cells due to the administration of the anti-CD4 antibody (FIG. 5).

3. Action Mechanism of Antitumor Effect by Use of Anti-CD4 Antibody Alone, Use of Anti-PD-1 Antibody or Anti-PD-L1 Antibody Alone, or Combined Use of Anti-CD4 Antibody+Anti-PD-1 Antibody or Anti-PD-L1 Antibody The mouse melanoma cell line B16F10 (5×10$^5$ cells/mouse) was subcutaneously transplanted into the right abdomen of C57BL/6 mice (female, 7 weeks old), and antibody administration was carried out as described below (Day 0=day of cancer cell transplantation).

TABLE 2

| | |
|---|---|
| Negative control group | No antibody is administered. |
| Anti-CD4 alone group | An anti-CD4 antibody (0.2 mg; GK1.5) is intraperitoneally administered twice on Day 5 and Day 9. |
| Anti-PD-1 or anti-PD-L1 alone group | An anti-PD-1 antibody (J43, manufactured by BioXcell) or anti-PD-L1 antibody (10F.9G2, manufactured by BioXcell) is intraperitoneally administered at a dose of 0.2 mg on Day 4, Day 8, Day 14, and Day 18, four times in total. |
| Anti-CD4 + anti-PD-1 or anti-PD-L1 combination group | An anti-CD4 antibody (0.2 mg; GK1.5) is intraperitoneally administered twice on Day 5 and Day 9, and an anti-PD-1 antibody (J43, manufactured by BioXcell) or an anti-PD-L1 antibody (10F.9G2, manufactured by BioXcell) is intraperitoneally administered at a dose of 0.2 mg on Day 4, Day 8, Day 14, and Day 18, four times in total. |

From the mice in each group, blood samples were collected on Day 14, and the ratios of PD-1$^+$ cells, CD44$^{hi}$ cells, and CD137$^+$ cells among the CD8$^+$ cells in the blood were investigated by flow cytometry analysis. The procedure was as follows.

Blood was collected from each mouse, and peripheral blood lymphocytes were obtained by the specific gravity centrifugation method. The peripheral blood lymphocytes were stained with an anti-CD45 antibody, anti-CD11b antibody, anti-CD19 antibody, anti-NK1.1 antibody, anti-CD8 antibody, anti-CD44 antibody (clone IM7), and anti-PD-1 antibody, and subjected to flow cytometry analysis of peripheral blood PD-1$^+$ CD44$^{hi}$ CD8$^+$ T cells. Further, staining with an anti-CD45 antibody, anti-CD11b antibody, anti-CD19 antibody, anti-NK1.1 antibody, anti-CD8 antibody, anti-CD44 antibody, and CD137 antibody was carried out to analyze peripheral blood CD137$^+$ CD44$^+$ CD8$^+$ T cells.

Before the staining with the antibodies described above, Fc receptors were blocked with an anti-mouse CD16/CD32 antibody (clone 2.4G2, BioXcell). The measurement was carried out with Gallios (Beckman Coulter), followed by analysis using FlowJo software (version 9.7.5; FlowJo, LLC). Dead cells were removed by staining with propidium iodide.

Figures 1, 6:
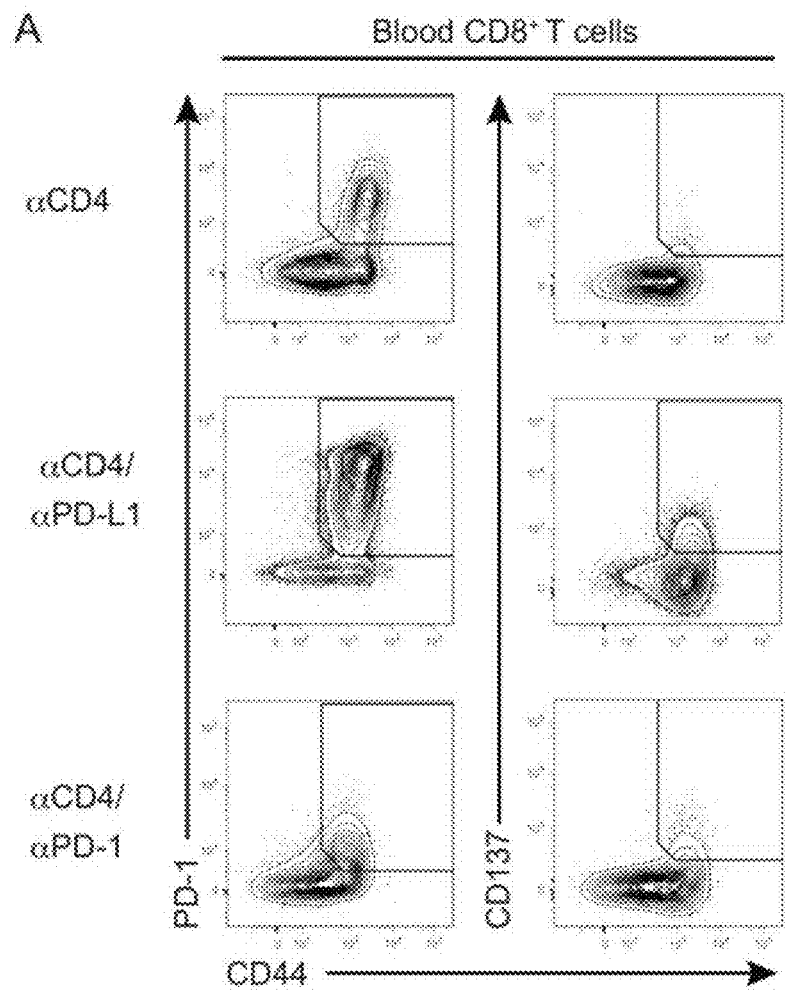
Figures 2, 6:
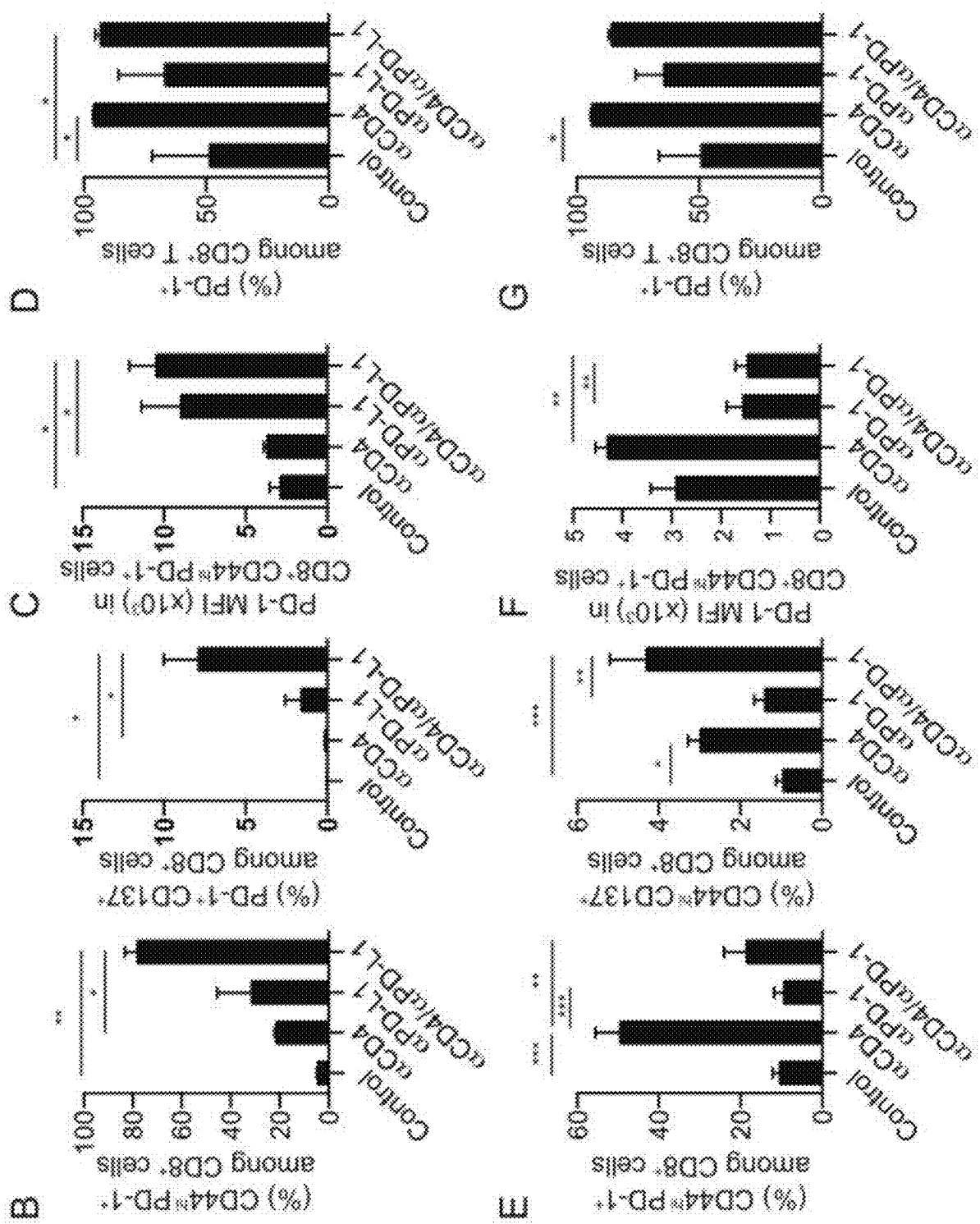

The results are shown in FIG. 6. It was remarkably shown that administration of an anti-CD4 antibody alone, combined administration of an anti-CD4 antibody and an anti-PD-1 antibody, or combined administration of an anti-CD4 antibody and an anti-PD-L1 antibody (clone 10F.9G2) increased PD-1$^+$ CD44$^{hi}$ CD8$^+$ T cells, CD137$^+$ CD44$^{hi}$ CD8$^+$ T cells, and PD-1$^+$ CD137$^+$ CD8$^+$ T cells.

From the mice in each group, the tumor was collected on Day 14, and intratumor mRNA was extracted, followed by investigation of the expression levels of the following genes by quantitative RT-PCR.

TNF-α (Tnf), IFN-γ (Ifng), Cxcl10, Cd274, Fasl, Prfl, and Granzyme (Gzmb)

Figure 7:
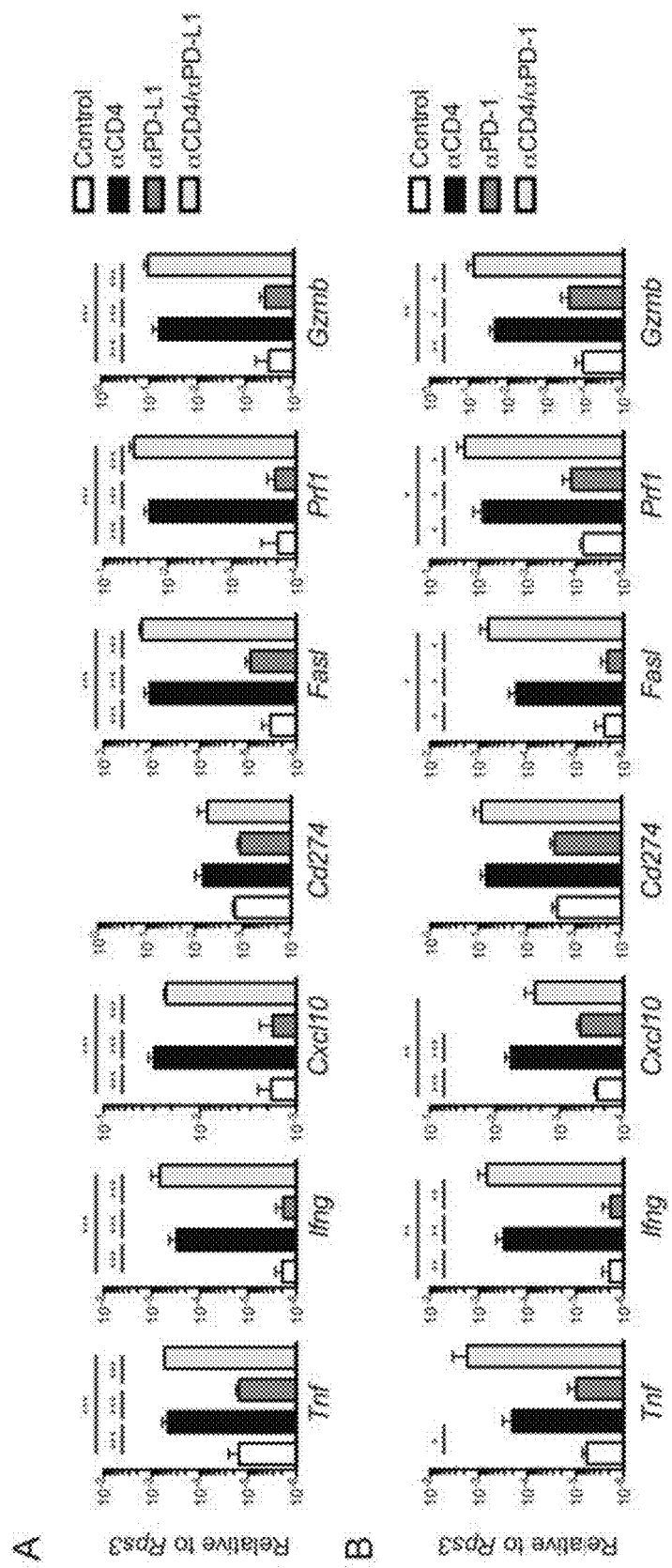
FIG. 7 shows the result of quantitative RT-PCR analysis of expression of various genes in the tumor tissue in B16F10 tumor-bearing mice to which an anti-CD4 antibody was administered alone, an immune checkpoint antibody (anti-PD-1 antibody or anti-PD-L1 antibody) was administered alone, or an anti-CD4 antibody+immune checkpoint antibody (anti-PD-1 antibody or anti-PD-L1 antibody) were administered in combination. A shows data obtained when the anti-PD-L1 antibody was administered, and B shows data obtained when the anti-PD-1 antibody was administered.

The results are shown in FIG. 7. It could be confirmed that administration of the anti-CD4 antibody caused high expression of humoral molecules, such as IFN-γ and granzyme, produced by effector cells including cytotoxic T cells. By this, the following action mechanism was strongly suggested: removal of CD4-positive cells→activation of CD8-positive cells and enhancement of their tissue infiltration→anti-tumor cell effect by activated effector cells (CTLs and the like).

The invention claimed is:

1. A method for testing in a patient a therapeutic effect of cancer therapy of a composition comprising an effective amount of anti-CD4 antibody having a cytotoxic activity to kill CD4-positive cells or an effective amount of anti-CD4 antibody or antigen binding fragment thereof which antibody or fragment comprises a cytotoxic component attached thereto to kill the CD4-positive cells, said method comprising:

obtaining a sample from the patient that has been administered said composition, wherein the sample comprises T cells,
    detecting
    (1) positive expression of at least one immune checkpoint receptor selected from the group consisting of PD-1, CD137, and TIM-3;
    (2) positive expression of CD8; and
    (3) high expression of at least one cell surface molecule selected from the group consisting of CD44 and CD45RO; on said T cells in said sample, and
    continuing administering the patient with said composition.

2. The method according to claim 1, wherein said (1) is PD-1.

3. The method according to claim 1 or 2, further comprising investigating expression of CD45RA on T cells, wherein said T cell population is negative for CD45RA.

4. The method according to claim 1, wherein said (1) is CD137.

5. The method according to claim 1, wherein said (1) is TIM-3.

6. The method according to claim 1, further comprising investigating expression of CD62L on T cells, wherein said T cell population shows low expression of CD62L.

7. The method according to claim 1, further comprising investigating expression of CCR7 on T cells, wherein said T cell population is negative for CCR7.

8. The method according to claim 1, wherein said sample is a blood sample.

9. The method according to claim 1, wherein said expression analysis is carried out by flow cytometry analysis.

10. The method according to claim 1, wherein the patient further has been administered at least one anticancer drug comprising as an effective ingredient an antibody against an immune checkpoint molecule.

* * * * *